(12) United States Patent
Maggi et al.

(10) Patent No.: US 9,101,627 B2
(45) Date of Patent: Aug. 11, 2015

(54) PHARMACEUTICAL COMPOSITIONS CONTAINING BRADYKININ ANTAGONISTS AND HYALURONIC ACID, AND USES THEREOF

(75) Inventors: Carlo Alberto Maggi, Florence (IT); Sandro Giuliani, Bagno a Ripoli (IT); Laura Quartara, Florence (IT)

(73) Assignee: ISTITUTO LUSO FARMACO D'ITALIA S.P.A., Peschiera Borromeo (IT)

( * ) Notice: Subject to any disclaimer, the term of this patent is extended or adjusted under 35 U.S.C. 154(b) by 797 days.

(21) Appl. No.: 12/743,891

(22) PCT Filed: Nov. 10, 2008

(86) PCT No.: PCT/EP2008/009451
§ 371 (c)(1),
(2), (4) Date: May 20, 2010

(87) PCT Pub. No.: WO2009/065507
PCT Pub. Date: May 28, 2009

(65) Prior Publication Data
US 2010/0292156 A1   Nov. 18, 2010

(30) Foreign Application Priority Data
Nov. 23, 2007   (IT) .............................. MI2007A2225

(51) Int. Cl.

| | |
|---|---|
| *A61K 31/728* | (2006.01) |
| *A61K 31/715* | (2006.01) |
| *A61P 19/02* | (2006.01) |
| *A61K 31/496* | (2006.01) |
| *A61K 9/00* | (2006.01) |
| *A61K 9/08* | (2006.01) |
| *A61K 38/08* | (2006.01) |
| *A61K 45/06* | (2006.01) |

(52) U.S. Cl.
CPC ............. *A61K 31/496* (2013.01); *A61K 9/0024* (2013.01); *A61K 9/08* (2013.01); *A61K 31/728* (2013.01); *A61K 38/08* (2013.01); *A61K 45/06* (2013.01)

(58) Field of Classification Search
CPC ..... A61K 31/728; A61K 31/496; A61K 9/08; A61K 45/06; A61K 2300/00
USPC ........... 514/54, 21.6, 16.8; 536/55.1, 53, 55.2
See application file for complete search history.

(56) References Cited

U.S. PATENT DOCUMENTS

2004/0022847 A1 * 2/2004 Leneau .......................... 424/452

FOREIGN PATENT DOCUMENTS

| WO | 03/103671 | 12/2003 |
|---|---|---|
| WO | 2006/040004 | 4/2006 |
| WO | WO 2006040004 A1 * | 4/2006 |

OTHER PUBLICATIONS

Gerwin et al. (Advanced Drug Delivery Reviews, (2006), vol. 58, pp. 226-242).*
Valenti et al. (The Journal of Pharmacology and Experimental Therapeutics, (2005), vol. 315. No. 2, pp. 616-623).*
Gerwin et al., "Intraarticular drug delivery in osteoarthritis" Advanced Drug Delivery Reviews, vol. 58, No. 2, May 20, 2006, pp. 226-242.

* cited by examiner

*Primary Examiner* — Shaojia Anna Jiang
*Assistant Examiner* — Michael C Henry
(74) *Attorney, Agent, or Firm* — Silvia Salvadori, P.C.

(57) ABSTRACT

Disclosed are pharmaceutical compositions containing, as the active ingredients, a mixture of a hyaluronic acid polymer with a bradykinin B2 receptor antagonist. Said compositions have proved especially effective in the treatment of degenerative joint diseases such as osteoarthritis using intra-articular injections.

15 Claims, No Drawings

PHARMACEUTICAL COMPOSITIONS CONTAINING BRADYKININ ANTAGONISTS AND HYALURONIC ACID, AND USES THEREOF

This application is a U.S. national stage of PCT/EP2008/009451 filed on Nov. 10, 2008, which claims priority to and the benefit of Italian Application No. MI2007A002225 filed on Nov. 23, 2007, the contents of which are incorporated herein by reference.

FIELD OF INVENTION

The invention relates to pharmaceutical compositions containing, as the active ingredients, a mixture of a hyaluronic acid polymer with a bradykinin B2 receptor antagonist. Said compositions have proved especially effective in the treatment of degenerative joint diseases such as osteoarthritis using intra-articular injections.

STATE OF THE ART

Osteoarthritis (OA), also known as degenerative joint disease, is a painful, progressive, degenerative disorder of the joints. The main pathophysiological characteristics of OA are destruction and loss of joint cartilage, hypertrophy, inflammation of the synovial membrane, and consequent swelling of the joint. These effects produce symptoms such as pain, stiffness and loss of function. The high incidence of OA in the elderly population, associated with the increase in average life expectancy, indicates that the number of patients affected by this disorder is likely to increase considerably in the near future. OA patients consider pain reduction to be very important to their quality of life.

No drugs which stop the progress of this disorder are currently available. The existing treatments are mainly designed to reduce the pain symptoms and regain the joint function. Paracetamol and non-steroidal anti-inflammatory drugs (NSAIDs) are widely prescribed for the treatment of pain in osteoarthritis. However, long-term use of said drugs can be accompanied by major adverse effects, especially at gastrointestinal level (ulcers) and in terms of platelet aggregation. Intra-articular injection of corticosteroids reduces the associated inflammation and pain, but they are rarely used as their effect is short-lived. There is consequently a clear need for new therapeutic agents that reduce the pain and inflammation associated with osteoarthritis.

Bradykinin (BK) is a member of the kinins, a family of small peptides (8-11 aminoacids) which derive from precursors with a high molecular weight (kininogens) following attack by enzymes with peptidase activity (kallikreins). Kinin formation is activated in various circumstances, involving inflammatory, ischaemic and immune processes or bacterial and viral infections.

Two kinin receptors have been pharmacologically characterised: the B1 receptor, which is minimally expressed under normal conditions, but whose expression is induced by the stimuli listed above, and the B2 receptor, which is constitutionally expressed by many cell types. Bradykinin, through stimulation of the B2 receptor, is one of the most important mediators of inflammation and pain, and is involved in the release of pro-inflammatory and hyperalgesic mediators.

It has been demonstrated that bradykinin (BK) participates in the pathophysiology of OA at various levels.

It has long been known that kinins are released into the synovial fluid of OA sufferers. Moreover, in these patients, the B2 receptor has been found in the cells lining the synovial cavity, the fibroblasts, and the endothelial cells of the blood vessels.

Many studies with various preclinical models indicate that BK, when administered by the intra-articular route, induces plasma extravasation and accumulation of neutrophils in the synovial membrane of the rat more effectively than other inflammation mediators such as substance P, histamine, and calcitonin gene-related peptide. Moreover, BK reduces the proteoglycans content in the joint cartilage and generates the release of prostaglandins in murine OA models.

Some bradykinin B2 receptor antagonists have proved effective in inhibiting inflammatory events and hyperalgesia in various animal synovitis models.

After its release, BK excites and sensitises the sensory nerve fibres that innervate the articular capsule.

The clinical significance of BK has been demonstrated in a phase II trial conducted on 58 patients with symptomatic OA of the knee, in which a single intra-articular administration of B2 receptor antagonist icatibant (90 µg/1 ml) reduced the intensity of pain in the knee to a greater extent than the placebo (55 patients). Sanofi-Aventis recently reported that in patients with OA of the knee, intra-articular infiltration of icatibant (3×500 µg injections one week apart) induces a strong analgesic response which lasts for up to 3 months after the treatment, and this considerable analgesic effect is obtained with negligible or no side effects.

Many bradykinin B2 receptor antagonists have been described in the literature.

EP370453 describes some compounds with a peptide structure which act as bradykinin antagonists, and said compounds include the one defined as icatibant. Icatibant also forms the subject of patent EP1594520, wherein its use in the prophylaxis and treatment of osteoarthritis is disclosed.

WO03103671 describes a group of very powerful non-peptide bradykinin antagonists. A selection of particularly potent antagonists is reported in WO2006040004, including the compound MEN16132; also these antagonists have proved highly effective in the prophylaxis and treatment of osteoarthritis, especially in intra-articular treatments of the knee.

Hyaluronan (also known as hyaluronic acid or hyaluronate) is a non-sulphated glycosaminoglycan widely distributed in the endothelial, connective, epithelial and neural tissues. It is one of the major components of extracellular matrix, and significantly contributes to cell proliferation and migration. On average, a person weighing 70 kg has 15 g of hyaluronan in the body, a third of which is exchanged (broken down and synthesised) every day.

Hyaluronan is one of the major components of synovial fluid, and increases its viscosity. Together with lubricin, it is one of the main lubricants of the fluid components. Hyaluronan is also an important component of joint cartilage, where it is found as the lining of each cell (chondrocytes).

Hyaluronan has long been used for treatment of OA of the knee (Puhl W; Scharf P (1997). *Ann Rheum Dis* 56 (7): 637-40.) Said treatment, known as viscosupplementation, consists of a series of injections into the knee joint which are designed to increase the viscosity of the fluids contained in it, lubricating and supporting the joint and consequently producing an analgesic effect. It has also been postulated that hyaluronan has a favourable biochemical effect on the cartilage cells. The first product of this kind to be launched on the market was Hylan G-F 20 (Synvisc®), which has been marketed by Genzyme since 1998. The European Medicines Agency (EMEA) extended the approval of Hylan GF-20 as a treatment for OA pain to the hip in 2002, and to the ankle and shoulder in 2007. Other products on the market include Ostenil® (TRB CHEMEDICA), Suplasyn® (MERCKLE RECORDATI) and GO-ON® (ROTTAPHARM).

A meta-analysis of 18 randomised clinical trials has confirmed the clinical benefits of Hylan G-F 20 and this class of viscosupplements, concluding that viscosupplements are superior to a placebo and that many of them are more effective than steroids in the treatment of pain associated with OA of the knee (Positive Synvisc Data Published by Cochrane Collaboration Source, Press Release 2005, May 5, Genzyme Corp).

Structurally, hyaluronan is a polymer consisting of repetitive disaccharide units of N-acetylglucosamine and sodium glucuronate. The one used for the treatment of OA is generally extracted from coxcombs, and fractions of various mean molecular weights, ranging from 0.5 to 10 million daltons, can be isolated. The viscosupplementation effect varies, depending on the molecular weight and density (Gomis et al, Arthritis & Rheumatism, 2004, 50:314-326).

Numerous methods have been proposed for the treatment of osteoarthritis, including the use of BK antagonists or hyaluronic acid.

WO03063799 also proposes the use of pharmaceutical compositions containing a plurality of chondroprotective agents, including matrix metal proteinase (MMP) inhibitors (bradykinin inhibits MMP production), but no mention is made of the use of hyaluronic acid.

However, there is an unmet need for effective treatments for degenerative joint diseases such as osteoarthritis.

DISCLOSURE OF THE INVENTION

It has now surprisingly been found that pharmaceutical compositions containing, as the active ingredients:
a) hyaluronic acid
b) a bradykinin B2 receptor antagonist
show surprising efficacy in the treatment of degenerative joint diseases such as, but not limited to, osteoarthritis.

The present invention relates to pharmaceutical compositions containing a bradykinin B2 receptor antagonist, the following ones being preferred:
H-D-Arg-Arg-Pro-Hyp-Gly-Igl-Ser-D-F5F-Igl-Arg-OH (B10056),
H-Arg-Arg-Pro-Hyp-Gly-Igl-Ser-D-Igl-Oic-Arg-OH (B9430),
H-D-Arg-Arg-Pro-Hyp-Gly-Thi-Ser-D-Tic-Oic-Arg-OH (Icatibant),
4-[2-[([[3-(3-Bromo-2-methyl-imidazo[1.2-a]pyridine-8-yl oxymethyl)-2,4-dichloro-phenyl]-methyl-carbamoyl]-methyl)-carbamoyl]-vinyl]-N,N-dimethyl-benzamide, (FR167344)
3-(6-Acetylamino-pyridine-3-yl)-N-([[2,4-dichloro-3-(2-methyl-quinoline-8-yl oxymethyl)-phenyl]-methyl-carbamoyl]-methyl)-acrylamide, (FR173657 or FK3657)
1-[2,4-Dichloro-3-(2,4-dimethyl-quinoline-8-yl oxymethyl)-benzene sulphonyl]-pyrrolidine-2-carboxylic acid [3-(4-carbamidoyl-benzoylamino)-propyl]-amide, (LF 160687, Anatibant)
4-(4-[1-[2,4-Dichloro-3-(2,4-dimethyl-quinoline-8-yl oxymethyl)-benzene sulphonyl]-pyrrolidine-2-carbonyl]-piperazine-1-carbonyl)-benzamidine, (LF160335)
2-[5-(4-Cyano-benzoyl)-1-methyl-1H-pyrrol-2-yl]-N-[2,4-dichloro-3-(2-methyl-quinoline-8-yl oxymethyl)-phenyl]-N-methyl-acetamide, or one of the compounds described in WO2006/04004, having general formula (I)

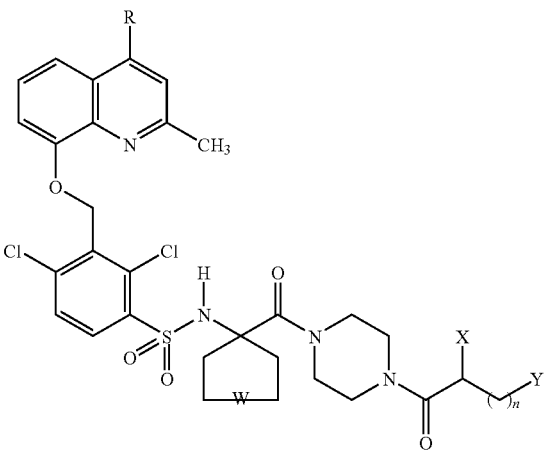

wherein
R is hydrogen or methyl
W represents a simple bond or an O atom
n=3, 4
X is hydrogen or a —NR1R2 amino group in which R1 and R2 can be independently of one another hydrogen or a group selected from methyl, ethyl n-propyl, isopropyl,
Y is a quaternary ammonium (—NR3R4R5)$^+$A$^-$ in which R3, R4, R5 can be independently of one another methyl, ethyl n-propyl, isopropyl, butyl, isobutyl, n-pentyl and A$^-$ is an anion of a pharmaceutically acceptable acid;
the pharmacologically acceptable salts, enantiomers and enantiomeric mixtures thereof.

For the purposes of this invention, a pharmaceutically acceptable acid is an acid selected from hydrochloric, hydrobromic, phosphoric, carbonic, acetic, sulphuric, trifluoroacetic, methansulphuric, succinic, maleic, malic, malonic, citric, edetic acid; where the anion carries two or more negative charges, A$^-$ shall be a fractional value.

Among the compounds of general formula (I), the following compound is particularly preferred: (4-(S)-Amino-5-(4-{4-[2,4-dichloro-3-(2,4-dimethyl-quinoline-8-yl oxymethyl)-benzenesulphonylamino]-tetrahydro-pyran-4-carbonyl}-piperazin-1-yl)-5-oxo-pentyl]-trimethyl-ammonium, in salified form with ions formally deriving from an acid selected from hydrochloric, acetic, sulphuric, trifluoroacetic, methanesulphonic, succinic and edetic acids; chloride dihydrochloride is the compound defined as MEN16132 (MW 871.5).

The hyaluronic acid used has a mean molecular weight between 0.5 and 10 million daltons, and preferably between 4 and 9 million daltons; absolutely preferred is the hyaluronic acid with a mean MW between 5 and 8 million daltons, as is or in the forms of the sodium or potassium salt.

The compositions according to the invention contain an amount of bradykinin antagonist per dose between $5.7 \times 10^{-5}$ and $2.3 \times 10^{-2}$ mmols (which, in the case of MEN16132, corresponds to an approximate amount of 0.05 to 20 mg), preferably between $1.1 \times 10^{-4}$ and $1.1 \times 10^{-2}$ mmols (which, in the case of MEN16132, corresponds to an approximate amount of 0.1 to 10 mg), and even more preferably between $2.9 \times 10^{-4}$ and $5.7 \times 10^{-3}$ mmols (which, in the case of MEN16132, corresponds to an approximate amount of 0.25 to 5 mg).

Said compositions also contain hyaluronic acid in the amount of 1 to 100 mg, and preferably 5 to 20 mg, per dose.

Pharmaceutical formulations according to this invention can also contain one or more pharmaceutically acceptable carriers/excipients.

Liquid and semisolid pharmaceutical forms suitable for topical administration, such as solutions, creams, gels or transdermal patches, are preferred; in particular, forms suitable for intra-articular or intrabursal injection, such as solutions, and transdermal application, such as semisolid forms like creams or gels and transdermal patches. The pharmaceutical form can also consist of a form wherein some or all of the components are in a dry form, possibly lyophilised, to be reconstituted with an aqueous solution or other suitable vehicle before use.

Said formulations can be produced by methods well-known in the state of the art using known excipients such as binders, disintegrants, fillers, stabilisers, diluents and colorants. They can also include delayed- or slow-release forms made with suitable polymers known in pharmaceutical technology.

Pharmaceutically acceptable carriers/excipients such as solvents, preservatives such as antioxidants and/or chelating agents and antimicrobials, isotonicity regulators, and buffer systems are preferred for the preparation of liquid forms suitable for injectable use.

Water is preferable as solvent, possibly with co-solvents such as glycols, or polyalcohols such as ethylene glycol.

Preservatives or chelating agents may also be used, sodium edetate and sodium metabisulphite being preferred, and antimicrobials, benzyl alcohol being preferred.

Sodium chloride or mannitol are particularly preferred as isotonicity regulators.

The preferred buffer systems can be the complex of salts for the phosphate and citrate buffer, preferably in the form of sodium or potassium salts.

In this invention, especially in the description of compounds with a peptide structure, the following abbreviations have been used for some non-natural amino acids: Nal=naphthyl-alanine; NMePhe=N-methyl-phenylalanine, Oic=Octahydroindol-2-carboxylic acid, Hyp=Hydroxyproline, Igl=aminoindanecarboxylic acid, Cpg=1-aminocyclopentanecarboxylic acid, Tic=1,2,3,4-tetrahydroisoquinoline-3-carboxylic acid, F5F=pentafluorophenylalanine, Typical examples of formulations according to this invention are:

1. Hyaluronic acid, sodium salt, with a mean molecular weight between 0.5 and 10 million daltons, 5-20 mg, MEN-16132 0.25-5 mg, in saline solution (0.9% NaCl), 0.1 N HCl q.s. to pH 4.5, water q.s. to 1 ml.
2. Hyaluronic acid, sodium salt, with a mean molecular weight between 0.5 and 10 million daltons, 5-20 mg, MEN-16132 0.25-5 mg, in saline solution (0.9% NaCl), 0.1 N HCl q.s. to pH 6, water q.s. to 1 ml.
3. Hyaluronic acid, sodium salt, with a mean molecular weight between 0.5 and 10 million daltons, 5-20 mg, MEN-16132 0.25-5 mg, in saline solution (0.9% NaCl), phosphate buffer (pH 6-8), water q.s. to 1 ml.
4. Hyaluronic acid, sodium salt, with a mean molecular weight between 0.5 and 10 million daltons, 5-20 mg, MEN-16132 0.25-5 mg, in saline solution (0.9% NaCl), citrate buffer (pH 6-8), water q.s. to 1 ml.
5. Extempore preparation obtained by dissolving MEN-16132, 0.25-5 mg, in lyophilised form, with a solution of hyaluronic acid, sodium salt (mean molecular weight between 0.5 and 10 million daltons, 5-20 mg), with phosphate buffer in saline solution (0.9% NaCl), water q.s. to 1 ml.
6. Hyaluronic acid, sodium salt, with a mean molecular weight between 0.5 and 10 million daltons 5-20 mg, icatibant (MW 1304.5) 0.37-6.5 mg, in saline solution (0.9% NaCl), phosphate buffer (pH 6-8), water q.s. to 1 ml.

The pharmaceutical compositions according to the invention are useful in the prophylaxis and treatment of inflammatory, autoimmune, traumatic and degenerative joint diseases such as osteoarthritis and post-traumatic osteoarthritis, degenerative osteoarthritis (gonarthritis, spondylarthritis); spondylosis, synovitis, tenosynovitis, bursitis, contusions, sprains, dislocations and subluxations, and in joint diseases caused by developmental alterations such as osteochondritis and dysplasia.

The dose can vary according to age and the patient's general state of health, the nature and gravity of the disease or disorder, and the route and type of administration. In the case of intra-articular use in an adult human patient, the use of the pharmaceutical compositions according to the invention could involve a weekly dose (in a single administration) of bradykinin antagonist amounting to between $2.9 \times 10^{-4}$ and $5.7 \times 10^{-3}$ mmols (which, in the case of MEN16132, corresponds to approx. 0.25 to 5 mg) and between 5 and 20 mg of hyaluronic acid.

The following examples illustrate the invention in greater detail:

Example 1

Hyaluronic acid, sodium salt, with a mean molecular weight of 6 million daltons, 10 mg, MEN16132 0.5 mg, in saline solution (0.9% NaCl), 0.1N HCl q.s. to pH 4.5, water q.s. to 1 ml. The solution is placed in pre-filled 2.25 ml syringes.

Example 2

Hyaluronic acid, sodium salt, with a mean molecular weight of 6 million daltons, 10 mg, MEN16132 0.5 mg, in saline solution (0.9% NaCl), containing phosphate buffer ($Na_2HPO_4$ 0.16 mg $NaH_2PO_4$ 0.04 mg), water q.s. to 1 ml. The solution is placed in pre-filled 2.25 ml syringes.

Example 3

Hyaluronic acid, sodium salt, with a mean molecular weight of 6 million daltons, 10 mg, MEN16132 0.2 mg, in saline solution (0.9% NaCl), 0.1N HCl q.s. to pH 4.5, water q.s. to 1 ml. The solution is placed in pre-filled 2.25 ml syringes.

Example 4

Hyaluronic acid, sodium salt, with a mean molecular weight of 6 million daltons, 10 mg, in saline solution (0.9% NaCl), containing phosphate buffer ($Na_2HPO_4$ 0.16 mg, $NaH_2PO_4$ 0.04 mg), water q.s. to 1 ml. MEN16132, in lyophilised form, is dissolved with the solution described above.

Example 5

Hyaluronic acid, sodium salt, with a mean molecular weight of 6 million daltons, 10 mg, icatibant 0.5 mg, in saline solution (0.9% NaCl), containing phosphate buffer ((Na$_2$HPO$_4$ 0.16 mg, NaH$_2$PO$_4$ 0.04 mg), water q.s. to 1 ml. The solution is placed in pre-filled 2.25 ml syringes.

Biological Activity

The activity of MEN16132, icatibant and hyaluronic acid was measured in an experimental model of osteoarthritis induced by intra-articular injection of sodium monoiodoacetate (MIA) which inhibits glycolysis in the chondrocytes, thus causing damage and death to those cells with consequent degeneration of the joint surface, in a very similar way to human osteoarthritis.

MIA (1 mg/25 µl) was injected into the intra-articular space of the right knee of the rat, while 25 µl of saline was administered to the left knee as internal control.

The administration of MIA causes pain, difficulty of walking and inability to bear weight on the paw corresponding to the treated knee; the weight of the body therefore falls mainly on the left paw, to an extent directly proportional to the pain perceived. This effect persists for many weeks. The imbalance in weight on the two weight-bearing paws, evaluated in a non-invasive way with the incapacitance test, measures the pain resulting from the joint damage (osteoarthritis) induced by MIA.

The purpose of this test was to evaluate the protective effect of bradykinin B2 receptor antagonists against experimental osteoarthritis, and to establish the effect of co-administration of hyaluronic acid.

Seven days after the treatment with MIA, the compounds under study were injected, and the test was repeated at various times to measure the painkilling effect and its duration.

MEN16132 and icatibant, at the dose of 3 µg/25 µl i.a., reduced the pain caused by osteoarthritis by 55% and 40% respectively; the maximal inhibitory effect was observed 3 days after administration of the compounds. No further significant increase in inhibitory effect was observed at the dose of 10 µg/25 µl i.a. The antinociceptive effect lasted for over a week with both compounds.

The administration of hyaluronic acid (molecular weight 6 million daltons, 50 µg/25 µl i.a.) produced a modest antinociceptive effect, reducing the pain response by 16%.

Co-administration of MEN16132 or icatibant with hyaluronic acid considerably boosted the antinociceptive response in the rats in which osteoarthritis was induced with MIA. MEN16132 or icatibant (3 µg/25 µl i.a.) and hyaluronic acid (50 µg/25 µl) reduced pain, measured as imbalance of body weight between the untreated paw and the treated paw, by 72% and 65% respectively. On the basis of direct observation of their motor activity, the motor behaviour of the rats treated with MEN16132 or icatibant and hyaluronic acid did not differ from that of the controls not suffering from osteoarthritis. The effect of the two B2 receptor antagonists after a single administration in association with hyaluronic acid also lasted longer, in some cases for over two weeks.

Morphological and histological tests were performed to obtain further confirmation of the surprising efficacy of the association with hyaluronic acid in reducing the symptoms and damage caused by osteoarthritis. 14 days after treatment with the association of MEN16132 or icatibant and hyaluronic acid, a substantial reduction (over 50%) in the damage present on the joint surface of the knee was observed, characterised by reduced loss of chondrocytes, glycosaminoglycan matrix and exposure of subarticular bone, with far superior results to the single administration of B2 antagonists or hyaluronic acid.

Moreover, the association is particularly interesting from the application standpoint, because kinin B2 receptor antagonists achieve the antinociceptive effect slowly but with a long duration, whereas hyaluronic acid with a high molecular weight (6 million daltons) or a salt thereof produces the maximum effect within a few hours of administration. The association disclosed in this invention is therefore rapidly effective and long-lasting due to the complementary and boosting effect of the two classes of compounds.

The invention claimed is:
1. Pharmaceutical composition for topical administration comprising a mixture of:
   a) hyaluronic acid or salts thereof selected from the group consisting of sodium and potassium; and
   b) a bradykinin B2 receptor antagonist together with pharmaceutically acceptable carriers and excipients, wherein:
(i) the hyaluronic acid is in polymer form with a mean MW between 0.5 and 10 million daltons,
(ii) the hyaluronic acid is in an amount of 1-100 mg per dose,
(iii) the bradykinin B2 receptor antagonist is selected from the group consisting of compounds of formula (I)

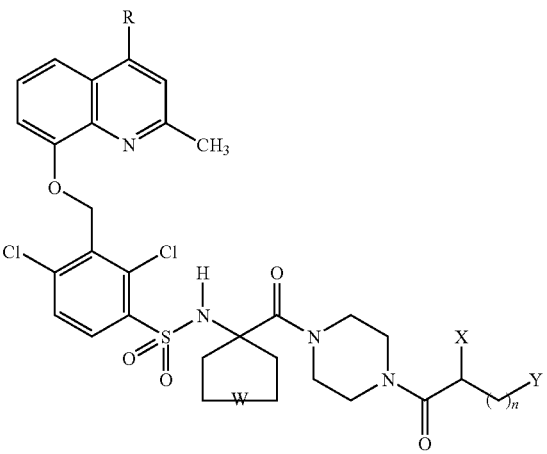

(I)

wherein
R is hydrogen or methyl
W represents a simple bond or an O atom
n=3, 4
X is hydrogen or a —NR1R2 amino group in which R1 and R2 can be independently of one another hydrogen or a group selected from methyl, ethyl n-propyl, isopropyl, and
Y is a quaternary ammonium (—NR3R4R5)$^+$A$^-$ in which R3, R4, R5 can be independently of one another methyl, ethyl n-propyl, isopropyl, butyl, isobutyl, n-pentyl and A$^-$ is an anion of a pharmaceutically acceptable acid;
the pharmacologically acceptable salts, enantiomers and enantiomeric mixtures thereof,
(iv) the bradykinin B2 receptor antagonist is in an amount of between $5.7 \times 10^{-5}$ and $2.3 \times 10^{-2}$ mMoles per dose, and
(v) the composition is in the form of an intra-articular or intrabursal injectable solution or a transdermal form selected from cream, gel or patch.

2. Pharmaceutical composition as claimed in claim 1, wherein the bradykinin B2 receptor antagonist is the compound of general formula (I): (4-(S)-amino-5-(4-{4-[2,4-dichloro-3-(2,4-dimethyl-quinoline-8-yl oxymethyl)-benzenesulphonylamino]-tetrahydro-pyran-4-carbonyl}-piperazin-1-yl)-5-oxo-pentyl)-trimethyl-ammonium in salified form with ions formally deriving from an acid selected from hydrochloric, acetic, sulphuric, trifluoroacetic, methanesulphonic, succinic and edetic acids.

3. Pharmaceutical composition as claimed in claim 2, wherein the compound (4-(S)-amino-5 (4-{4-[2,4-dichloro-3-(2,4-dimethyl-quinoline-8-yl oxymethyl)-benzenesulphonylamino]-tetrahydro-pyran-4-carbonyl}-piperazin-1-yl)-5-oxo-pentyl)-trimethyl-ammonium is in the form of chloride dihydrochloride.

4. Pharmaceutical composition as claimed in claim 1, wherein the amount of hyaluronic acid per dose is 5-20 mg.

5. Pharmaceutical composition as claimed in claim 1, wherein the mean MW of the hyaluronic acid ranges between 4 and 9 million daltons.

6. Pharmaceutical composition as claimed in claim 5, wherein the mean MW of the hyaluronic acid ranges between 5 and 8 million daltons.

7. Pharmaceutical composition as claimed in claim 1, wherein the amount of bradykinin B2 receptor antagonist is between $1.1 \times 10^{-4}$ and $1.1 \times 10^{-2}$ mMoles per dose.

8. Pharmaceutical composition as claimed in claim 7, wherein the amount of bradykinin B2 receptor antagonist is between $2.9 \times 10^{-4}$ and $5.7 \times 10^{-3}$ mmols per dose.

9. Pharmaceutical composition as claimed in claim 1, wherein the bradykinin antagonist is in a solid form selected from crystalline, amorphous or lyophilised, to be dissolved before use in a solution containing hyaluronic acid so as to constitute the intra-articular or intrabursal injectable solution.

10. Pharmaceutical composition as claimed in claim 1, also containing a buffer selected from phosphate or citrate.

11. Pharmaceutical composition as claimed in claim 1, also containing sodium chloride as isotonicity regulator.

12. Pharmaceutical composition as claimed in claim 1, also containing sodium edetate as preservative and chelating agent.

13. Pharmaceutical composition as claimed in claim 1, wherein said amount of bradykinin B2 receptor antagonist corresponds to an amount of 0.05 to 20 mg per dose of (4-(S)-amino-5-(4-{4-[2,4-dichloro-3-(2,4-dimethyl-quinoline-8-yl oxymethyl)-benzenesulphonylamino]-tetrahydro-pyran-4-carbonyl}-piperazin-1-yl)-5-oxo-pentyl)-trimethyl-ammonium chloride dihydrochloride.

14. Pharmaceutical composition as claimed in claim 7, wherein said amount of bradykinin B2 receptor antagonist corresponds to an amount of 0.1 to 10 mg per dose of (4-(S)-amino-5-(4-{4-[2,4-dichloro-3-(2,4-dimethyl-quinoline-8-yl oxymethyl)-benzenesulphonylamino]-tetrahydro-pyran-4-carbonyl}-piperazin-1-yl)-5-oxo-pentyl)-trimethyl-ammonium chloride dihydrochloride.

15. Pharmaceutical composition as claimed in claim 8, wherein said amount of bradykinin B2 receptor antagonist corresponds to an amount of 0.25 to 5 mg per dose of (4-(S)-amino-5-(4-{4-[2,4-dichloro-3-(2,4-dimethyl-quinoline-8-yl oxymethyl)-benzenesulphonylamino]-tetra-hydro-pyran-4-carbonyl}-piperazin-1-yl)-5-oxo-pentyl)-trimethyl-ammonium chloride dihydrochloride.

* * * * *